United States Patent
Tsui

(10) Patent No.: US 11,419,407 B2
(45) Date of Patent: Aug. 23, 2022

(54) DRY-CLEANING BRUSH

(71) Applicant: DONG GUAN LONG XIANG BRUSHES LTD, Dongguan (CN)

(72) Inventor: Mingcheong Tsui, Dongguan (CN)

(73) Assignee: DONG GUAN LONG XIANG BRUSHES LTD, Dongguan (CN)

( * ) Notice: Subject to any disclaimer, the term of this patent is extended or adjusted under 35 U.S.C. 154(b) by 699 days.

(21) Appl. No.: 16/411,166

(22) Filed: May 14, 2019

(65) Prior Publication Data

US 2019/0261768 A1 Aug. 29, 2019

Related U.S. Application Data

(63) Continuation of application No. PCT/CN2016/108032, filed on Nov. 30, 2016.

(30) Foreign Application Priority Data

Nov. 15, 2016 (CN) .......................... 201611001325.7

(51) Int. Cl.
*A46B 11/00* (2006.01)
*A61K 8/02* (2006.01)
*A61Q 5/02* (2006.01)
*A45D 24/22* (2006.01)
*A01K 13/00* (2006.01)

(52) U.S. Cl.
CPC ........ *A46B 11/0037* (2013.01); *A01K 13/001* (2013.01); *A45D 24/22* (2013.01); *A46B 11/001* (2013.01); *A46B 11/0062* (2013.01); *A46B 11/0086* (2013.01); *A61K 8/022* (2013.01); *A61Q 5/02* (2013.01); *A46B 2200/104* (2013.01)

(58) Field of Classification Search
CPC ........ A46B 11/0037; A46B 2200/1066; A46B 11/0062; A46B 2200/104; A46B 11/0086; A46B 11/001; A45D 19/02; A45D 24/22; A61K 8/022; A61Q 5/02
USPC ......................................................... 132/121
See application file for complete search history.

(56) References Cited

FOREIGN PATENT DOCUMENTS

GB 002237734 A * 5/1991 ............. A46B 13/02
WO WO 2008/107243 A1 * 9/2008 ............. A61H 23/02

OTHER PUBLICATIONS

English translation of the Patent CN 200953929 Y (dated Mar. 1, 2022).*

* cited by examiner

*Primary Examiner* — Eisa B Elhilo
(74) *Attorney, Agent, or Firm* — Hemisphere Law, PLLC; Zhigang Ma

(57) ABSTRACT

A dry-cleaning brush includes a body, a base plate and a bristle component. A storage cavity used for storing shampoo powder is formed between the body and the base plate. A powdering device is arranged in the storage cavity and includes a pressing rod arranged on the base plate, lever assemblies, pistons, and at least one leaking hole formed in the base plate, and the pistons are located at openings of the leaking holes. Each lever assembly includes a lever having two ends respectively clamped on the pressing rod and the corresponding piston. A rebound mechanism is arranged between an elastic gland, the pressing rod and the base plate. The powdering device controls the pistons based on the lever principle, the elastic gland and the pressing rod are pressed to drive the levers to pull the pistons away from the leaking holes.

9 Claims, 3 Drawing Sheets

DRY-CLEANING BRUSH

BACKGROUND OF THE INVENTION

1. Technical Field

The invention relates to the field of combing brushes, in particular to a dry-cleaning brush used for shampoo powder.

2. Description of Related Art

With the progress of human society and the continuous improvement of the living standard of people, hair brushes are used for washing hairs in bathes particularly by those having long hair so as to better comb and clean hair. However, in water-deficient areas where people have little washing water due to severe water resource shortage, dry shampoo powder is used to clean hair so as to keep the hair clean without using water, particularly in cases where the hair of certain pets cannot be washed with water, the hair of certain special populations cannot be washed with water for the time being, and too much hair grease is secreted after a long journey while hair washing with water is not available. However, existing shampoo powder is sprayed or smeared on hair for cleaning, but cannot be uniformly applied to hair, and consequentially, the hair cannot be sufficiently cleaned; and meanwhile, traditional combs are used for assistance when shampoo powder is sprayed or smeared on hair for cleaning, and consequentially, using is inconvenient.

BRIEF SUMMARY OF THE INVENTION

The objective of the invention is to overcome the defects of the prior art by providing a dry-cleaning brush used for shampoo powder. The dry-cleaning brush is provided with a storage cavity used for storing shampoo powder, and the shampoo powder can be applied to hair by pressing an elastic gland when the dry-cleaning brush is used for combing hair. The dry-cleaning brush is a practical hair dry-cleaning tool particularly in cases where the hair of certain pets cannot be washed with water, the hair of certain special populations cannot be washed with water for the present, and too much hair oil is secreted after a long journey while hair washing with water is unavailable.

According to the technical solution provided by the invention to fulfill the above objective, the dry-cleaning brush comprises a body, a base plate and a bristle component. A storage cavity used for storing shampoo powder is formed between the body and the base plate. A powdering device is arranged in the storage cavity and comprises an elastic gland arranged on the body, a pressing rod arranged on the base plate, lever assemblies, pistons, and at least one leaking hole formed in the base plate. The pistons are located at openings of the leaking holes. Each lever assembly comprises a lever having two ends respectively clamped on the pressing rod and the corresponding piston. A rebound mechanism is arranged between the pressing rod and the base plate.

Furthermore, each lever is composed of a gripper part, a connecting part and a clamping part which are connected in sequence, wherein the gripper part and the clamping part are respectively arranged at two ends of the lever, a recess is formed in a length direction and allows the pressing rod to be clamped therein, a rotary shaft extending towards two sides is arranged on the connecting part in a width direction, a support used for supporting the rotary shaft is arranged on the base plate, a joint of the rotary shaft and the support serves as a fulcrum of the lever, and the clamping part is composed of two pressing blocks distributed in a C shape and a lifting block.

Furthermore, a T-shaped pull rod is arranged on an upper portion of each piston, is connected to the corresponding clamping part, and has a horizontal end clamped between the corresponding pressing blocks and the corresponding lifting block as well as a vertical end clamped in a clamping groove formed in the middle of the corresponding lifting block; and the base plate is provided with guide tubes around the leaking holes, and lower portions of the pistons are pulled by the levers to move along the guide tubes.

Furthermore, the base plate is provided with pits used for gathering the shampoo powder towards the leaking holes, with the leaking holes as centers; and through holes are formed in junctions of the side walls of the guide tubes and the pits, and insides and outsides of the guide tubes are communicated through the through holes.

Furthermore, the pressing rod is composed of a pressing part, a neck part and a movable part which are connected in sequence, wherein the longitudinal section of the neck part is in an I shape, the middle of the neck part is clamped in the recesses of the gripper parts of the levers, the base plate is concavely provided with a stationary tube towards the storage cavity, the movable part is inserted into the stationary tube, a check ring is fixed to an end face of the movable part, and a check block used for preventing the check ring from moving towards the storage cavity is arranged at an opening of the stationary tube.

Furthermore, the movable part is sleeved with a spring, one end of the spring abuts against the lower end of the neck part, the other end of the spring abuts against the opening of the stationary tube, and a seal ring is arranged between the opening of the stationary tube and the spring; and the pressing rod, the stationary tube and the spring form the rebound mechanism.

Furthermore, a riveting part used for fixing the check ring is arranged on the end face of the movable part, and the riveting part is a rivet or a screw.

Furthermore, the body is a box-like shell having an end provided with an opening, the base plate is fixed to the opening of the body, a feed inlet is formed in the other end, opposite to the open end, of the body, a soft elastic gland is arranged at the feed inlet, and the lower end of the elastic gland is clamped on the pressing part of the pressing rod.

Furthermore, the bristle component is detachably mounted on the other side, backing onto the body, of the base plate and is provided with a plurality of bristles, and powder discharging channels are formed in positions, corresponding to the leaking holes of the base plate, of the bristle component.

Furthermore, the bristle component is a wool bristle component or a plant bristle component.

The invention has the following beneficial effects: shampoo powder used for cleaning hair is stored in the storage cavity formed between the body and the base plate, the powdering device is arranged in the storage cavity and controls the pistons based on the lever principle, the elastic gland and the pressing rod are pressed to drive the levers to pull the pistons away from the leaking holes, and then the shampoo powder in the storage cavity falls between the bristles of the bristle component along the leaking holes and is applied to hair when the brush is used for combing hair, so that uniform dry-cleaning of hair with the shampoo powder is achieved, and water resources are saved.

Figure 1:
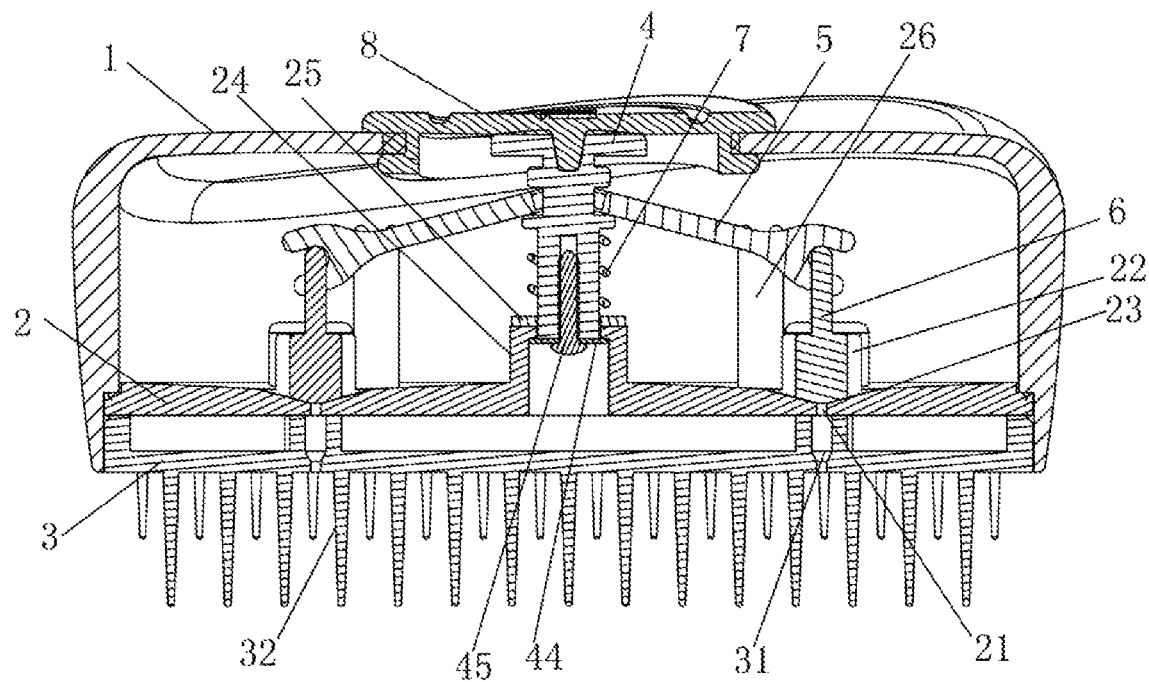
FIG. 1 is a sectional view of the invention.

In the figures: 1, body; 2, base plate; 21, leaking hole; 22, guide tube; 221, through hole; 23, pit; 24, stationary tube; 25, seal ring; 26, support; 3, bristle component; 31, powder discharging channel; 32, bristles; 4, pressing rod; 41, pressing part; 42, neck part; 43, movable part; 5, lever; 51, gripper part; 52, connecting part; 53, clamping part; 531, pressing block; 532, lifting block; 6, piston, 61, pull rod; 7, spring; 8, elastic gland; 9, plant bristle component.

DETAILED DESCRIPTION OF THE INVENTION

A detailed description of the invention is given below with reference to FIGS. 1-5.

As shown in FIGS. 1-4, a dry-cleaning brush comprises a body 1, a base plate 2 and a bristle component 3. A storage cavity used for storing shampoo powder is formed between the body 1 and the base plate 2. A powdering device is arranged in the storage cavity and comprises an elastic gland 8 arranged on the body 1, a pressing rod 4 arranged on the base plate 2, lever assemblies, pistons 6, and two leaking holes 21 symmetrically formed in the base plate 2, wherein the pressing rod 4 is located at the center of the storage cavity, the two lever assemblies are symmetrically arranged on two sides of the pressing rod 4, and the pistons 6 corresponding to the two leaking holes 21 are respectively connected with the two lever assemblies; the pistons 6 are located at openings of the leaking holes 21. Each lever assembly comprises a lever 5 having two ends respectively clamped on the pressing rod 4 and the corresponding piston 6. A rebound mechanism is arranged between the pressing rod 4 and the base plate 2. The elastic gland 8 can be opened to add shampoo powder into the storage cavity or be integrally sealed and is in linkage with the pistons 6 of the base plate 2.

Figure 3:
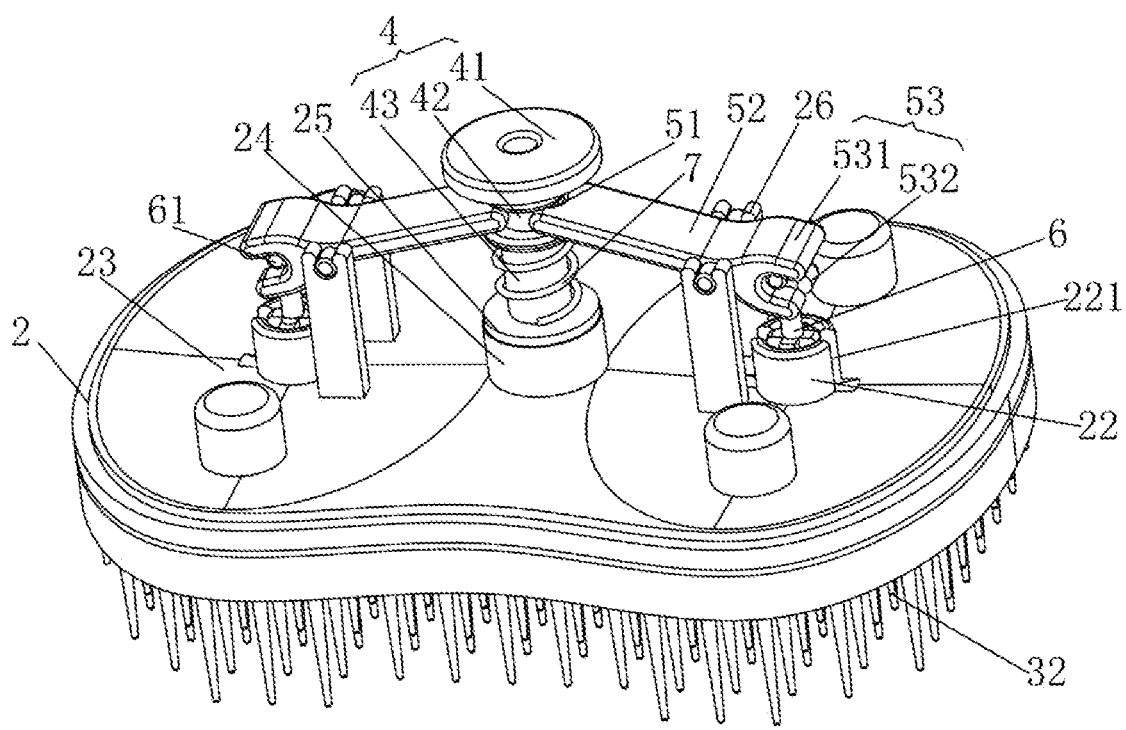
FIG. 3 is an internal view of the invention.
Figure 4:
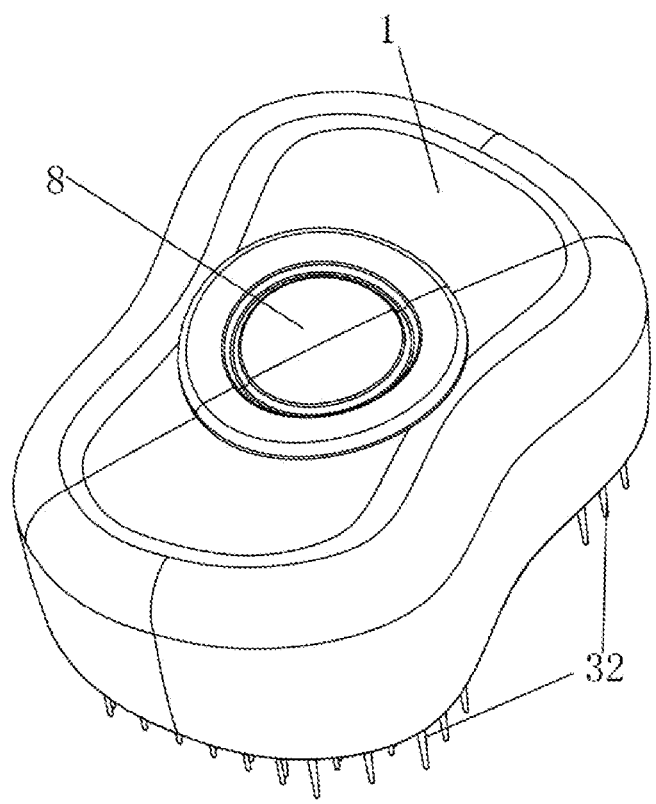
FIG. 4 is an overall view of the invention.

Wherein, as shown in FIG. 1 and FIG. 3, each lever 5 is composed of a gripper part 51, a connecting part 52 and a clamping part 53 which are connected in sequence, wherein the gripper part 51 and the clamping part 53 are respectively arranged at two ends of the lever 5; a recess is formed in a length direction and allows the pressing rod 4 to be clamped therein; a rotary shaft extending towards two sides is arranged on the connecting part 53 in a width direction, and a support 26 used for supporting the rotary shaft is arranged on the base plate 2, and a joint of the rotary shaft and the support 26 serves as a fulcrum of the lever 5; and the clamping part 53 is composed of two pressing blocks 531 distributed in a C shape and a lifting block 532.

Wherein, as shown in FIG. 1 and FIG. 3, each piston 6 has an upper portion provided with a T-shaped pull rod 61 and a lower portion provided with a main body having a cross-shaped cross section, wherein the pull rod 61 is connected to the corresponding clamping part 53, a horizontal end of the pull rod 61 is clamped between the corresponding pressing blocks 531 and the corresponding lifting block 532, and a vertical end of the pull rod 61 is clamped in a clamping groove formed in the middle of the corresponding lifting block 532. The base plate 2 is provided with guide tubes 22 located around the leaking holes 21. The main bodies of the lower portions of the pistons 6 are pulled by the levers 5 to move along the guide tubes 22.

Wherein, as shown in FIG. 3, the base plate 2 is provided with pits 23 used for gathering the shampoo powder towards the leaking holes 21, with the leaking holes 21 as centers; and a pair of through holes 221 are symmetrically formed at a junction of the side wall of each guide tube 22 and the corresponding pit 23 and are used for communicating the inside of the guide tube 22 with the outside of the guide tube 22.

Wherein, as shown in FIG. 1 and FIG. 3, the pressing rod 4 is composed of a pressing part 41, a neck part 42 and a movable part 43 which are connected in sequence, wherein the longitudinal section of the neck part 42 is in an I shape, and the middle of the neck part 42 is clamped in the recesses of the gripper parts 51 of the levers 5; the base plate 2 is convexly provided with a stationary tube 24 towards the storage cavity, the movable part 43 is inserted into the stationary tube 24, a check ring is fixed to an end face of the movable part 43, and a check block used for preventing the check ring from moving towards the storage cavity is arranged at an opening of the stationary tube 24.

Wherein, the movable part 43 is sleeved with a spring 7, one end of the spring 7 abuts against the lower end of the neck part 42, the other end of the spring 7 abuts against the opening of the stationary tube 24, and a seal ring 25 is arranged between the opening of the stationary tube 24 and the spring 7; and the pressing rod 4, the stationary tube 24 and the spring 7 form the rebound mechanism.

Wherein, a riveting part used for fixing the check ring is arranged on the end face of the movable part 43, and the riveting part is a screw.

Wherein, the body 1 is a box-like shell having an end provided with an opening. The base plate 2 is fixed to the opening of the body 1. A feed inlet is formed in the other end, opposite to the open end, of the body 1. A soft elastic gland 8 is arranged at the feed inlet and has a lower end clamped on the pressing part 41 of the pressing rod 4.

Figure 5:
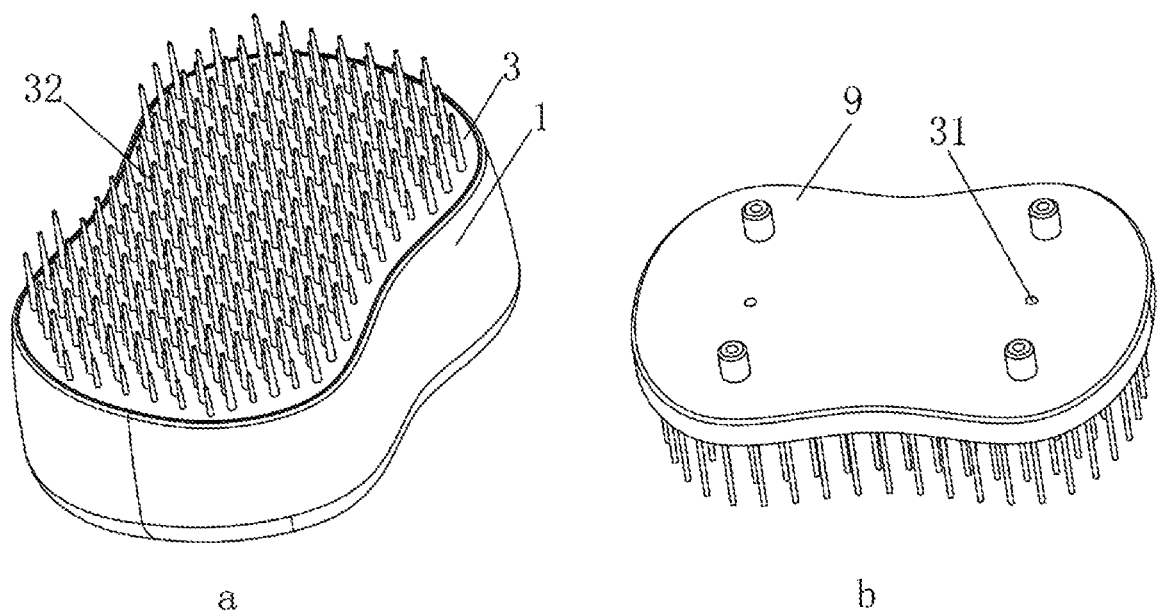
FIG. 5 is a structural view of a bristle component of the invention.

Wherein, as shown in FIG. 5, the bristle component 3 is detachably mounted on the other side, backing onto the body 1, of the base plate 2 and is provided with a plurality of bristles 32. Powder discharging channels 31 are formed in positions, corresponding to the leaking holes 21 of the base plate 2, of the bristle component 3. In FIGS. 1-4 and in FIG. 5a, the bristle component 3 is a wool bristle component which can be replaced with a plant bristle component 9 shown in FIG. 5b or other bristle components, so that the application range of the dry-cleaning brush is widened, the dry-cleaning brush can adapt to different types of hair and be suitable for more hair qualifies or hair styles.

As shown in FIG. 1, when the dry-cleaning brush is not stressed, the pressing rod 4 moves upwards along the stationary tube 24 under the effect of an elastic force of the spring 7 and drives the gripper parts 51 of the levers 5 to tile upwards, the clamping parts 53 of the levers 5 move downwards under the effect of the levers 5, the pressing blocks 531 of the clamping parts 53 press the pistons 6 downwards along the guide tubes 22, and thus, the leaking holes 21 are blocked.

Figure 2:
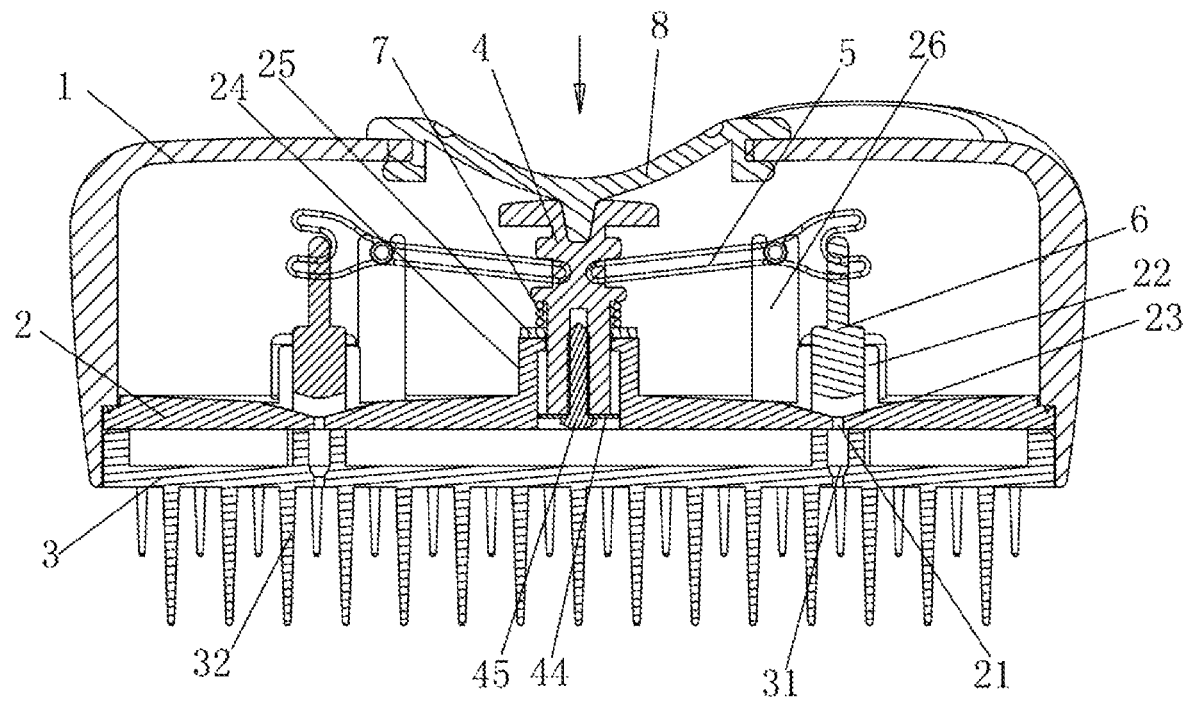
FIG. 2 is a sectional view of an elastic gland in a stressed and pressed state of the invention.

As shown in FIG. 2, when the dry-cleaning brush is used, shampoo powder used for cleaning hair is placed into the storage cavity between the body 1 and the base plate 2 via the feed inlet in the body 1, the powdering device arranged in the storage cavity and controls the pistons based on the lever 5 principle, the elastic gland 8 and the pressing rod 4 are pressed to drive the gripper parts 51 of the levers 5 to move downwards, then the clamping parts 53 of the levers 5 are tilted upwards to pull the pistons 6 away from the leaking holes 21, the shampoo powder gathered in the pits 23 of the storage cavity falls between the bristles 32 of the bristle component 3 sequentially through the through holes 221 of the guide tubes 22, the leaking holes 21, and the powder discharging channels 31 of the bristle component 3 and is then is applied to hair when the dry-cleaning brush is used for combing hair, so that uniform dry-cleaning of the hair with the shampoo powder is achieved, and water resources are saved.

The above embodiments are not intended to limit the technical scope of the invention. Any modifications, equivalent variations and embellishments of the above embodiments according to the technical essence of the invention should also fall within the technical scope of the invention.

What is claimed is:

1. A dry-cleaning brush, comprising a body, a base plate and a bristle component, wherein a storage cavity used for storing shampoo powder is formed between the body and the base plate, a powdering device is arranged in the storage cavity and comprises an elastic gland arranged on the body, a pressing rod arranged on the base plate, lever assemblies, pistons, and at least one leaking hole formed in the base plate, and the pistons are located at openings of the leaking holes; each said lever assembly comprises a lever having two ends respectively clamped on the pressing rod and the corresponding piston; a rebound mechanism is arranged between the pressing rod and the base plate; the base plate is provided with guide tubes around the leaking holes, and lower portions of the pistons are pulled by the levers to move along the guide tubes; the base plate is provided with pits used for gathering the shampoo powder towards the leaking holes, with the leaking holes as centers; and through holes are formed in junctions of side walls of the guide tubes and the pits, and insides and outsides of the guide tubes are communicated through the through holes.

2. The dry-cleaning brush according to claim 1, wherein each said lever is composed of a gripper part, a connecting part and a clamping part which are connected in sequence, wherein the gripper part and the clamping part are respectively arranged at two ends of the lever, a recess is formed in a length direction and allows the pressing rod to be clamped therein, a rotary shaft extending towards two sides is arranged on the connecting part in a width direction, a support used for supporting the rotary shaft is arranged on the base plate, a joint of the rotary shaft and the support serves as a fulcrum of the lever, and the clamping part is composed of two pressing blocks which are distributed in a C shape and a lifting block.

3. The dry-cleaning brush according to claim 2, wherein a T-shaped pull rod is arranged on an upper portion of each said piston, is connected to the corresponding clamping part, and has a horizontal end clamped between the corresponding pressing blocks and the corresponding lifting block and a vertical end clamped in a clamping groove formed in a middle of the corresponding lifting block.

4. The dry-cleaning brush according to claim 2, wherein the pressing rod is composed of a pressing part, a neck part and a movable part which are connected in sequence, a longitudinal section of the neck part is in an I shape, and a middle of the neck part is clamped in the recesses of the gripper parts of the levers; and the base plate is provided with a stationary tube towards the storage cavity, the movable part is inserted into the stationary tube, a check ring is fixed to an end face of the movable part, and a check block used for preventing the check ring from moving towards the storage cavity is formed at an opening of the stationary tube.

5. The dry-cleaning brush according to claim 4, wherein the movable part is sleeved with a spring, the spring has an end abutting against a lower end of the neck part and an end abutting against the opening of the stationary tube, and a seal ring is arranged between the opening of the stationary tube and the spring; and the pressing rod, the stationary tube and the spring form the rebound mechanism.

6. The dry-cleaning brush according to claim 4, wherein a riveting part used for fixing the check ring is arranged on the end face of the movable part, and the riveting part is a rivet or a screw.

7. The dry-cleaning brush according to claim 4, wherein the body is a box-like shell having an end provided with an opening, the base plate is fixed to the opening of the body, a feed inlet is formed in an end, opposite to an open end, of the body, and a soft elastic gland is arranged at the feed inlet and has a lower end clamped on the pressing part of the pressing rod.

8. The dry-cleaning brush according to claim 1, wherein the bristle component is detachably mounted on a side, backing onto the body, of the base plate and is provided with a plurality of bristles; and powder discharging channels are formed in positions, corresponding to the leaking holes, of the bristle component.

9. The dry-cleaning brush according to claim 8, wherein the bristle component is a wool bristle component or a plant bristle component.

* * * * *